United States Patent
Semmlow

(10) Patent No.: US 9,320,489 B1
(45) Date of Patent: Apr. 26, 2016

(54) APPARATUS FOR DETECTION OF CARDIAC ACOUSTIC SIGNALS

(71) Applicant: John Leonard Semmlow, New Brunswick, NJ (US)

(72) Inventor: John Leonard Semmlow, New Brunswick, NJ (US)

(*) Notice: Subject to any disclaimer, the term of this patent is extended or adjusted under 35 U.S.C. 154(b) by 0 days.

(21) Appl. No.: 14/945,369

(22) Filed: Nov. 18, 2015

Related U.S. Application Data

(63) Continuation of application No. 14/552,842, filed on Nov. 25, 2014, now Pat. No. 9,226,726.

(51) Int. Cl.
*A61B 7/04* (2006.01)
*A61B 7/02* (2006.01)
*A61B 5/00* (2006.01)

(52) U.S. Cl.
CPC ............. *A61B 7/04* (2013.01); *A61B 5/6823* (2013.01); *A61B 7/026* (2013.01); *A61B 2562/0204* (2013.01)

(58) Field of Classification Search
CPC ........... A61B 7/14; A61B 5/0093; A61B 7/02
USPC ........................................................ 600/528
See application file for complete search history.

(56) References Cited

U.S. PATENT DOCUMENTS

| | | | |
|---|---|---|---|
| 4,672,976 A * | 6/1987 | Kroll | 600/528 |
| 5,036,857 A | 8/1991 | Semmlow et al. | |
| 5,109,863 A | 5/1992 | Semmlow et al. | |
| 5,595,188 A | 1/1997 | Kassal | |
| 5,807,268 A | 9/1998 | Reeves et al. | |
| 5,827,198 A | 10/1998 | Kassal | |
| 5,885,222 A | 3/1999 | Kassal | |
| 5,913,829 A | 6/1999 | Reeves et al. | |
| 6,152,879 A | 11/2000 | Mohler | |
| 6,261,237 B1 | 7/2001 | Swanson et al. | |
| 6,278,890 B1 | 8/2001 | Chassaing et al. | |
| 7,520,860 B2 | 4/2009 | Guion-Johnson et al. | |
| 7,998,091 B2 * | 8/2011 | Carim et al. | 600/586 |
| 8,024,974 B2 | 9/2011 | Bharti et al. | |
| 8,333,718 B2 | 12/2012 | Carim et al. | |
| 8,715,206 B2 | 5/2014 | Telfort et al. | |

OTHER PUBLICATIONS

Wang, P., Tie, B., Welkowitz, W., Semmlow, J., and Kostis, J. "Modeling Sound Generation in Stenosed Coronary Arteries." Biomedical Engineering, vol. 35, No. 3, pp. 367-374, Mar. 2007.

(Continued)

*Primary Examiner* — Paula J Stice
(74) *Attorney, Agent, or Firm* — Marc D. Lowy

(57) ABSTRACT

The present invention is an apparatus for detection of high-frequency heart sounds for diagnosing heart diseases. One embodiment utilizes an accelerometer-based detector that presents a light load to the chest, is sensitive to the desired high frequency range, and provides a quantitative measurement of the quality of the acquired signal. Two pairs of flexible beams, each having piezoelectric transducers on the upper and lower surfaces are supported by a lightweight mechanical structure. The beams are center-loaded so that they respond to the same mechanical energy and will produce identical electrical signals in the absence of noise. Through additional signal processing means the two signals can provide an estimate of the signal-to-noise ratio of the acquired signal. The two signals can also be combined to further improve the signal-to-noise ratio. The invention is designed to be light weight, sensitive to higher frequencies, and to be relatively immune to noise.

16 Claims, 6 Drawing Sheets

(56) References Cited

OTHER PUBLICATIONS

Semmlow J.L., Welkowitz W., Kostis J., and MacKenzie J.W., "Coronary artery disease-correlates between diastolic auditory characteristic and coronary artery stenosis," IEEE Trans. Biomed. Eng., vol. BME-30, pp. 136-139, 1983.

Semmlow, J., and Rahalkar, K., "Acoustic detection of coronary artery disease," Annual Rev of Biomed, Engr. vol. 9: pp. 449-469, Apr. 2007.

Vermarien, H,. Vollenjoven, E. 1984. The recording of heart vibrations: a problem of vibration measurement on soft tissue. Med. Biol. Eng. Comput. vol. 22, pp. 168-178.

Padmanahban, V., and Semmlow J., Accelerometer type cardiac transducer for detection of low-level heart sounds. IEEE Trans. Biomed Engr. vol. BME-40, pp. 21-28,1993.

Akay, Y.M., Akay, MA., Welkowitz, W., Semmlow, J.L., and Kostis, J.B., "Noninvasive detection of coronary artery disease: A comparative study of signal processing methods," IEEE Trans. Biomed. Engr. vol. 40, pp. 571-578, 1993.

* cited by examiner

APPARATUS FOR DETECTION OF CARDIAC ACOUSTIC SIGNALS

CROSS REFERENCE TO RELATED APPLICATION(S)

This application is a continuation-in-part of U.S. patent application Ser. No. 14/552,842 filed Nov. 25, 2014, which is incorporated by reference as if fully set forth.

FIELD OF INVENTION

The present invention relates to an apparatus for detection of high-frequency heart sounds for diagnosing heart diseases, and more particularly, a noninvasive cardiac acoustic detector which provides high quality, low noise acoustic signals useful for diagnosis of coronary artery disease.

BACKGROUND

There are devices presently available to detect acoustic signals from the chest each having its own advantages and disadvantages as described in the review by Semmlow and Rahalkar. The motivation for most of these devices is the detection of sound signatures associated with coronary artery disease as originally described by Semmlow el al. in 1983. Coronary artery disease results from occlusions or blockages of the coronary arteries which supply blood to the heart. Such blockages will produce turbulent blood flow including an auditory correlate. Theoretical studies by Wang et al indicate that said auditory correlates will be at relatively high frequencies: above 200 Hz and as high as 1 kHz. Such sounds are generally too faint and at too high a frequency to be heard through a traditional stethoscope, although murmurs associated with coronary artery disease have occasionally been reported. Acoustic detection of the sounds produced by blood flowing through partially occluded coronary arteries would thereby enable the noninvasive detection of this major disease.

Devices for the detection of cardiac sounds from the chest fall into two broad categories: those that reference the acoustic energy to fixed positions on the chest and those that use an inertial reference; i.e., accelerometers. Most of the existing devices to measure sounds from the chest are chest-referenced such as described in U.S. Pat. Nos. 6,152,879, 6,261,237, and 7,520,860. Some chest-reference microphones have been constructed in arrays of multiple microphones as described in U.S. Pat. Nos. 6,278,890 and 7,037,268. It is also possible to combine multiple sensors to improve the signal level as described in U.S. Pat. No. 8,715,206. Chest-referenced devices require a mechanical means for stabilizing the sensor on the chest which places a relatively heavy mechanical load on the chest. Modified chest-referenced microphones have been constructed using flexible piezoelectric sensors which are attached directly to the chest using some type of temporary adhesive as described in U.S. Pat. Nos. 5,807,268, 5,595,188, 5,827,198, 5,885,222 and 5,913,829. In this approach, differential movements of the chest under the flexible piezoelectric sensor act as a self-reference.

All such chest-referenced devices must of necessity place a moderate-to-heavy load on the chest. Moreover, traditional microphone designs are sensitive to ambient noise from the environment. Flexible adhesive sensors are less sensitive to ambient noise and induce the lightest load, but they do not detect compression waves and are less sensitive to shear waves. Moreover, in addition to the weight of these sensors, there is still considerable mechanical loading as the chest must force flexing in these sensors in order to detect the bioacoustic energy. Mechanical loading decreases the sensitivity of the detection apparatus particularly to high-frequency acoustic signals as documented by Vermarien and Vollenhoven. To improve the sensitivity of chest referenced microphones, efforts to match the acoustic impedance of the microphone to the chest have been attempted as described in U.S. Pat. Nos. 6,152,879 and 6,278,890. While such impedance matching techniques may improve the power transferred to the microphone, they actually reduce signal level and still place a load on the chest.

Studies using chest reference microphones have not shown the ability to consistently detect the acoustic signatures associated with coronary artery disease as summarized in Semmlow and Rahalkar. An accelerometer-based sensor described by Padmanahban et al. and in U.S. Pat. Nos. 5,036,857 and 5,109,863 has produced signals that were moderately successful in detecting coronary artery disease as shown by Akay et al. Other accelerometer-based sensors have been described in U.S. Pat. Nos. 7,998,091, 8,024,974, and 8,333,718. Although these detectors will present a reduced mechanical load on the chest compared to chest-referenced devices, they are still comparatively heavy. Even moderate loads of 10-15 gm produced by these devices will reduce their ability to detect the acoustic signature of coronary artery disease as documented by Vermarien and Vollenhoven.

Since mechanical loading the chest will reduce the bioacoustic signal, particularly at high frequencies, there is a clear need for an acoustic detector which presents a very light mechanical load to the chest. Specifically, the detector should be less than 10 gm so as to be sensitive to the relatively high frequency signals in the range of 200 to 1200 Hz. Said detector should also be relatively immune to ambient or environmental noise.

The quality of the signal produced by any cardiac microphone will also depend on microphone position and attachment to the chest along with patient factors such as body weight. Hence the quality of signals produced by any detector will vary from patient-to-patient and even measurement-to-measurement. The signals produced by all cardiac microphones developed thus far provide no feedback on the quality of the detected signal. There is therefore a clear need for a cardiac acoustic detector that provides high quality, low noise signals over the range of desired frequencies, and that is capable of providing real-time information on the quality of the signal being detected, when used in conjunction with signal processing apparatus. The present invention accomplishes these objectives.

SUMMARY

The present invention is an apparatus for detection of high-frequency heart sounds for diagnosing coronary artery disease. One embodiment of the invention utilizes an accelerometer-based detector that presents a very light load to the chest, is sensitive to the desired high frequency range, and with additional signal processing means provides a quantitative measurement of the quality of the acquired signal.

It is therefore a primary objective of the invention to be very light in weight so as to present a minimum mechanical load to the chest. It is another objective of the invention to have a sensor mechanism that is very sensitive to mechanical energy in the desired frequency range of 200 to 1200 Hz and minimizes electrical interference. Another objective of the invention is to provide signals that allow the determination of signal quality as a measurement of the signal-to-noise ratio of the detected signal, where a signal is defined as the acoustic energy from the chest and where noise is defined as electrical noise from the transducer, electronics, or electrical interference from the environment. It is yet another aspect of this invention to be relatively immune to ambient or environmental acoustic noise by having an accelerometer-type design that is inherently immune to such artifacts.

In view of these objectives, one embodiment of this invention comprises two thin bending beams that support mechanically sensitive transducers positioned so they are sensitive to bending moments. In another aspect of the invention, these bending beams are supported at each end by a lightweight mechanical structure and said bending beams are center-loaded by the same low-mass weight so that they respond to the same mechanical energy and will produce identical signals in the absence of noise. In another aspect of this invention, each of the two bending beams includes two mechanically sensitive transducers that produce a bipolar signal that is differentially combined in the sensor electronics to reduce electrical interference.

In another embodiment of this invention, only a single bending beam is used that includes upper and lower mechanically sensitive transducers each producing a separate signal. In this alternate embodiment, the bending beam is supported at each end by a lightweight mechanical structure and said bending beam is center-loaded by a low-mass weight. In this embodiment, the upper and lower mechanically sensitive transducers produce separate single-ended, unipolar signals. If one of these single-ended signals is inverted, the two signals can be used in conjunction with additional signal processing means to provide a measurement of data quality.

Other features and advantages of the present invention will become apparent from the following more detailed description, taken in conjunction with the accompanying drawings, which illustrate, by way of example, the principles of the invention.

BRIEF DESCRIPTION OF THE DRAWING(S)

The foregoing Summary as well as the following detailed description will be readily understood in conjunction with the appended drawings which illustrate embodiments of the invention. In the drawings.

DETAILED DESCRIPTION OF ILLUSTRATIVE EMBODIMENT(S)

The present invention is an apparatus 10 for detection of high-frequency heart sounds for diagnosing coronary artery disease. One embodiment of this invention comprises an accelerometer-based cardiac acoustic detector 10 that converts bio-acoustic information to electrical signals while presenting a very light load to the chest, and providing sensitivity to the desired high frequency range. The benefits produced by the invention 10 include, in various embodiments, electrical output signals that may be further processed to provide quantitative measurements of the quality of electrical signals produced by a patient's cardiac bio-acoustic information.

Figure 1:
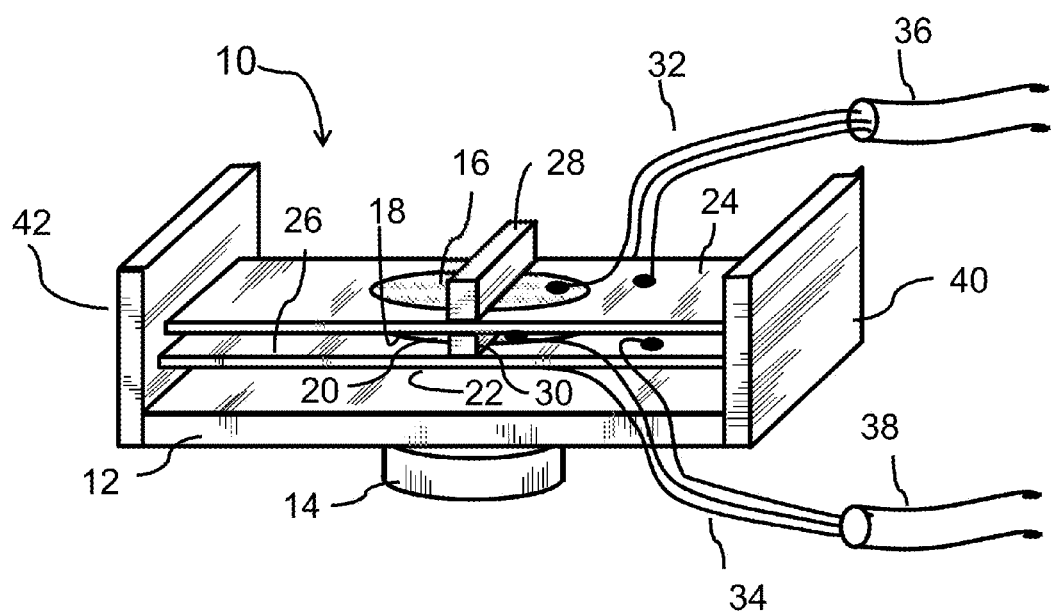
FIG. 1 is a top perspective view illustrating one embodiment of a cardiac acoustic detector.

FIG. 1 illustrates one embodiment of the invention 10 comprising an accelerometer type cardiac acoustic detector 10 that converts bio-acoustic information produced by a human heart to two electrical signals 36, 38 representing the same bio-acoustic information.

In some embodiments, the cardiac acoustic detector 10 comprises an accelerometer type acoustic detector 10 including single, dual, or multiple sensors that produce electrical signals representing the cardiac bio-acoustic information. In some embodiments of the accelerometer detector 10, the sensors comprise two low-mass, substantially planar, flexible bending beams 24,26 that each support two mechanically sensitive transducers 16,18,20,22. Said bending beams 24,26 are attached on each side to lightweight support walls 40,42. The right support wall 40 and a left support wall 42 are in turn supported by support frame 12.

The two bending beams, an upper bending beam 24 and a lower bending beam 26, are coupled at the center by a coupling element 30, so both bending beams 24,26 are subject to the same bending action. A coupling element 30 couples the influence of a low-mass weight 28 to the lower bending beam 26. Both bending beams 24,26 are center-loaded by at least one low-mass weight 28, such that the bending beams 24,26 respond similarly to accelerations produced by vibrations of the user's chest.

Figure 6:
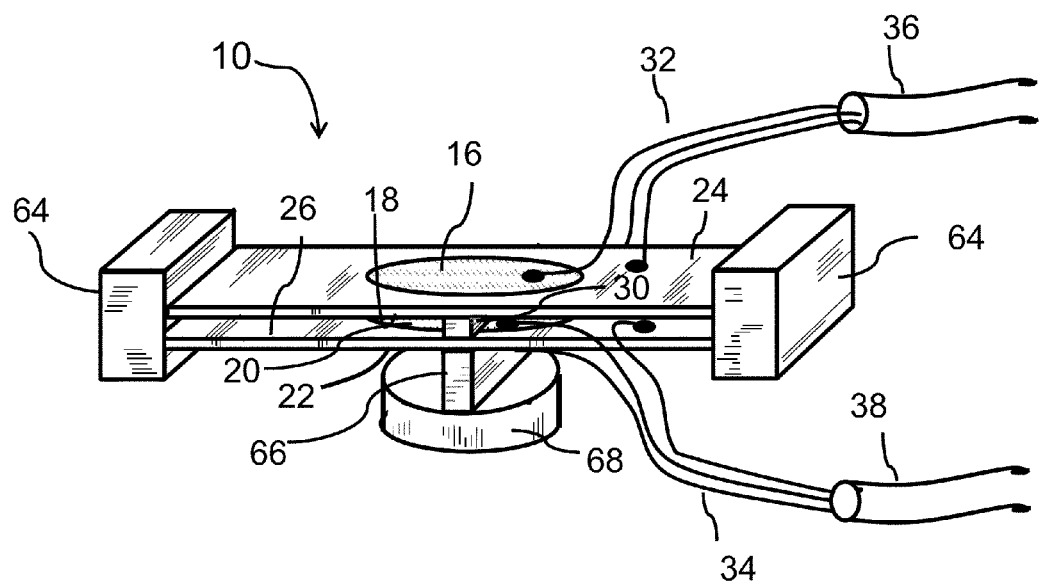
FIG. 6 is a top perspective view illustrating one embodiment of a cardiac acoustic detector including end-loaded weights.

In FIG. 6 is illustrated an end-loaded cardiac detector embodiment. A center loaded configuration provides a more compact configuration than some other embodiments, but in an end-loaded embodiment each bending beam 24,26 could be end-loaded with low-mass weights 64 and supported through support frame 66 and patient contact plate 68.

The support frame 12 is mechanically connected to the patient's chest through a patient contact plate 14 that extends below the support frame 12. The patient contact plate 14 may be comprised of the same material as the base frame and walls in some embodiments of the invention 10. In other embodiments a padded patient contact plate 14 could be used. Firm attachment of the patient contact plate 14 to the patient's chest is assured through the use of a viscous gel, double-sided tape, or other temporary adhesive (not shown). The patient contact plate 14 is configured so that a patient's chest vibrations deflect the bending beams 24,26 in accordance with the patient's heart vibrations.

Figure 2:
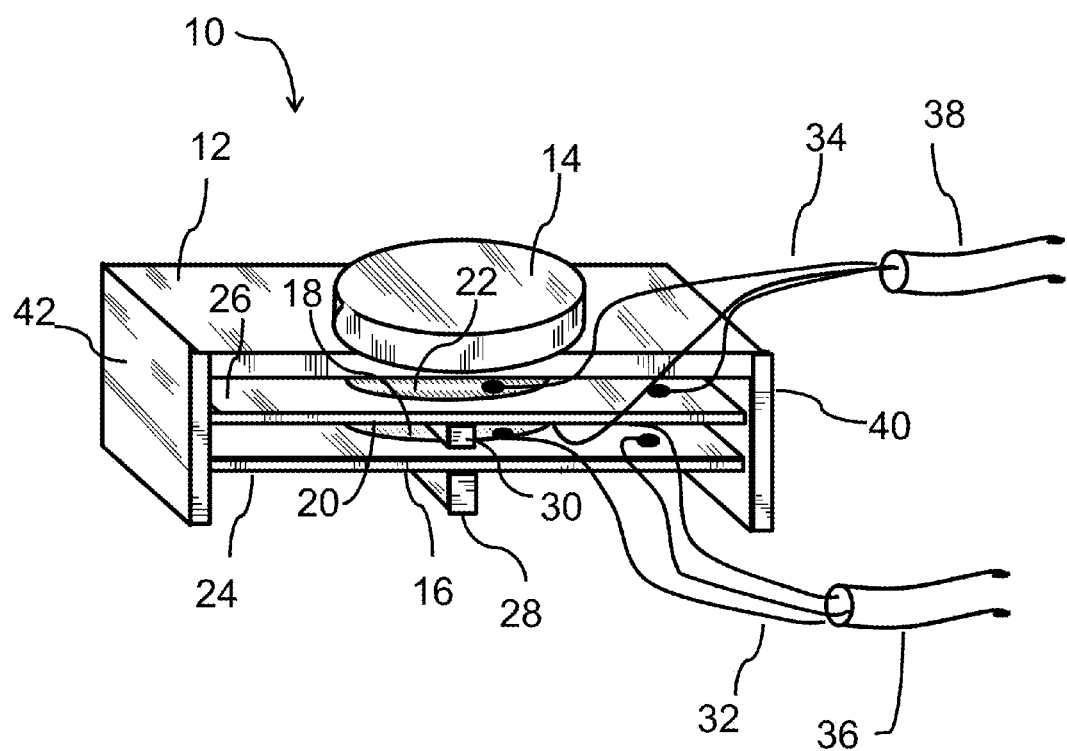
FIG. 2 is a bottom perspective view illustrating one embodiment of a cardiac acoustic detector.

FIG. 2 illustrates one embodiment of the invention 10 as seen from a bottom perspective view. The lower mechanically sensitive transducers 18,22 can be seen in this view. In some embodiments, the accelerometer type cardiac acoustic detector 10 may comprise single, dual, or multiple sensors that produce electrical signals representing the cardiac bio-acoustic information. In some embodiments of the cardiac acoustic detector 10, the sensors comprise two low-mass, substantially planar, flexible bending beams 24,26 supporting mechanically sensitive transducers 16,18,20,22 attached on each side to lightweight support walls 40,42. The right support wall 40 and a left support wall 42 are in turn supported by support frame 12.

The two bending beams, an upper bending beam 24 and a lower bending beam 26, are coupled at the center by a coupling element 30, so both bending beams 24,26 are subject to the same bending action. A coupling element 30 couples the influence of a low-mass weight 28 to the lower bending beam 26. Both bending beams 24,26 are center-loaded by at least one low-mass weight 28, such that the bending beams 24,26 respond similarly to accelerations produced by vibrations of the user's chest.

The support frame 12 is mechanically connected to the patient's chest through a patient contact plate 14 that extends below the support frame 12. The patient contact plate 14 may be comprised of the same material as the base frame and walls in some embodiments of the invention 10. In other embodiments a padded patient contact plate 14 could be used. Firm attachment of the patient contact plate 14 to the patient's chest is assured through the use of a viscous gel, double-sided tape, or other temporary adhesive (not shown). The patient contact plate 14 is configured so that a patient's chest vibrations deflect the bending beams 24,26 in accordance with the patient's heart vibrations.

In FIGS. 1-2, in some embodiments of the invention, the bending beams 24,26 may be substantially planar wherein each beam includes an upper mechanically sensitive transducer 16,20 and a lower mechanically sensitive transducer 18,22, located proximate to the low-mass weight 28. The mechanically sensitive transducers 16,20, 18,22 may in some embodiments be substantially disc shaped, and in other embodiments the mechanically sensitive transducers 16,20, 18,22 may be substantially rectangular in shape. In another embodiment, only a single bending beam 24 is present containing upper and lower mechanically sensitive transducers 16,20 each producing a unipolar signal 36,38.

The low-mass weight 28 may be comprised of lead, steel, or other metal in some embodiments of the invention 10. In an alternative embodiment (FIG. 5), the weight 28 consist of a built in preamplifiers 60 shown with connecting wires 62 to the mechanical transducers 16,20,18,22. In accordance with one of the embodiments of the invention, the thickness of the two bending beams 24,26 is adjusted to produce resonant frequencies of approximately 1000 Hz, so as to maximize the signal produced at the higher frequencies.

The upper bending beam 24 and lower bending beam 26 are deflected by the mass weight 28 extending across the upper bending beam 24, that in some embodiments is comprised of lead or other heavy metal. In another embodiment, the mass weight could comprise miniaturized electronics components preforming the function of the transducer preamplifiers 60 (FIG. 54). The force produced by the mass weight is transmitted to the lower bending beam 26 through coupling beam 30 which is placed between the bending beams 24,26. The support frame 12 and walls 40,42 are constructed using a strong but light material that in some embodiments is comprised of titanium, plastic, or even balsa wood.

The low-mass bending beams 24,26 comprise accelerometer detectors and are configured for increased sensitivity at high frequencies. In some embodiments, the bending beams 24,26 are configured to have a resonant frequency in the range of 800 to 1200 Hz so as to provide increased sensitivity to high frequency heart sounds.

The bending beams 24,26 in some embodiments of the invention 10 are comprised of aluminum, spring steel, or other flexible metal. In one embodiment of the invention 10, each bending beam 24,26 contains a mechanically sensitive transducer 16,20,18,22 comprised of piezoelectric materials on the upper surfaces of the bending beams 24,26 and similar piezoelectric materials on the lower surfaces of the flexible bending beams 24,26. When each flexible bending beam 24,26 bends, the piezoelectric element on one surface is in tension while the piezoelectric element on the opposite surface is in compression, thereby producing differential electrical signals. In another embodiment of the invention 10, only a single bending beam is used where the upper and lower piezoelectric transducers produce two single-ended signals.

Cardiac acoustic signals are output on two shielded cables 36,38 that supply differential sensor outputs 32,34 from the mechanically sensitive transducers 16,18,20,22 attached to the flexible bending beams 24,26.

In other embodiments, the bending beams 24,26 could support various mechanically sensitive materials including piezoelectric ceramics, piezoelectric crystals, piezoelectric film (e.g., PVDF2 film), piezo-resistive material, or strain gages.

Figure 3:
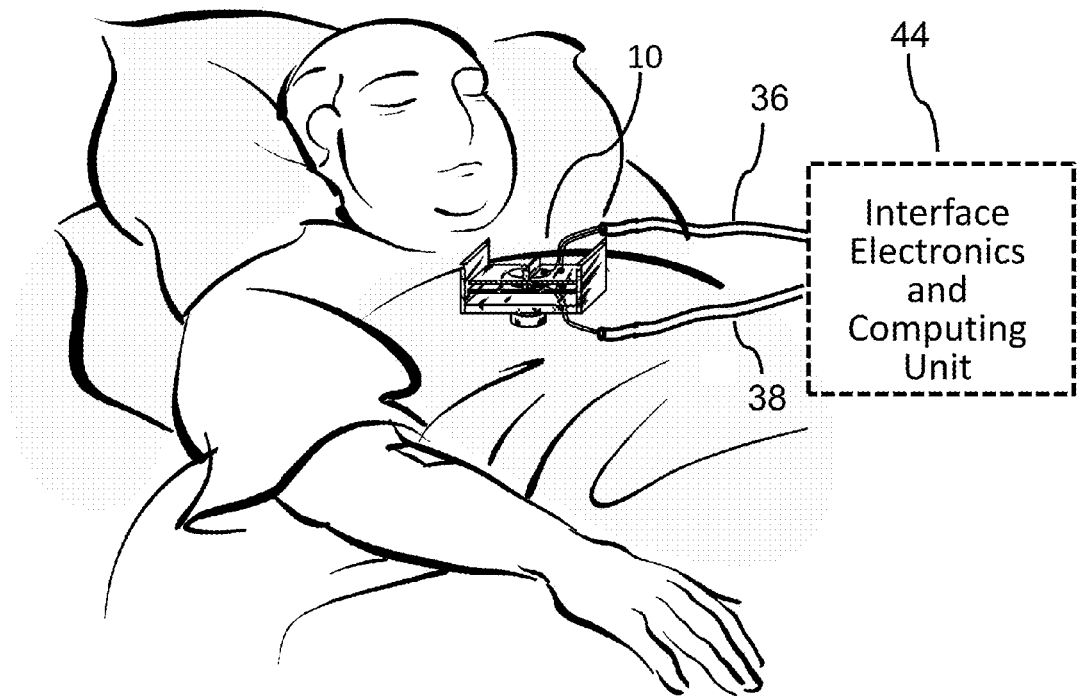
FIG. 3 is a front perspective view illustrating the placement of a cardiac acoustic detector on a patient.

FIG. 3 illustrates the placement of the cardiac acoustic detector 10 attached to the chest of a cardiac patient. The acoustic detector 10 is affixed to the patient using a viscous gel, double-sided tape, or other temporary adhesive (not shown). Cardiac acoustic signals from the acoustic detector 10 are output on two shielded cables 36,38 that are connected to differential sensor outputs. The output signals from the cardiac acoustic detector 10 are sent to an electronics interface and computing unit 44 via the shielded cables 36,38. The electronics interface and computing unit 44 performs signal processing functions on the signals received via the shielded cables 36,38.

Figure 4:
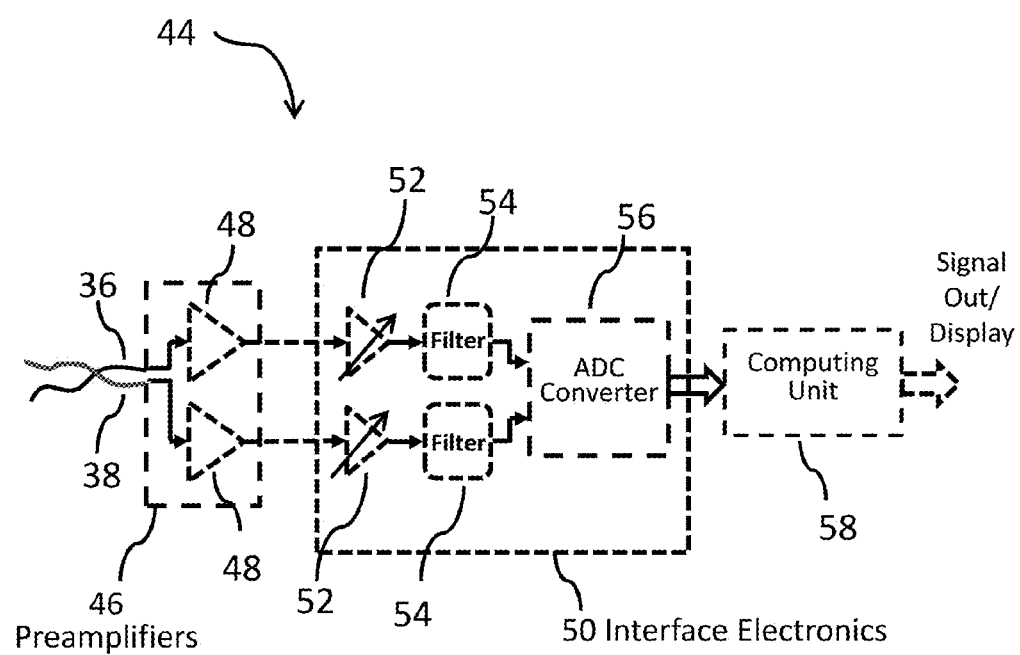
FIG. 4 is a block diagram illustrating external electronic components configured to provide a measurement of signal quality.

FIG. 4 illustrates electronic components, external to the invention 10, that can be configured to provide a measurement of the signal data quality provided by the invention 10. The shielded cables 36,38 are connected to an external electronics unit 44 that performs signal processing functions on the received cardiac signals. Differences in the two signals can then be converted by signal processing means into a measurement of signal quality.

In the absence of electronic noise, cardiac acoustic output signals 32, 34 received from the cardiac acoustic detector 10 by a preamplifier unit 46 should be identical. The preamplifier unit 46 is placed close to the acoustic detector unit 10 to minimize noise pickup. The preamplifiers 48 provide initial amplification for low level signals from the acoustic detector unit 10. The interface electronics unit 50 provides signal conditioning for the analog signal and analog-to-digital conversion. Adjustable gain amplifiers 52 provide variable amplification for the two signals. Lowpass filters 54 for the two signals prevent aliasing due to sampling by the analog-to-digital converter 56. The analog-to-digital converter 56 converts the two analog signals to digital format. The computing unit 58 implements additional signal processing software that includes evaluation of signal quality.

Figure 5:
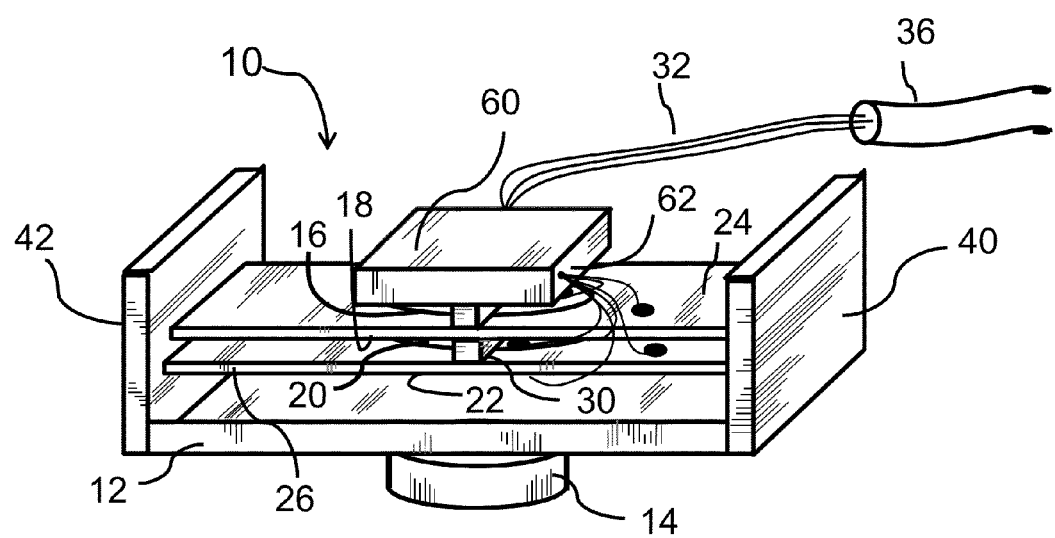
FIG. 5 is a top perspective view illustrating one embodiment of a cardiac acoustic detector including a preamplifier also serving as a center-loaded low-mass weight.

FIG. 5 illustrates one embodiment of the invention 10, including a built-in preamplifier 60 functioning also as a center-loaded low-mass weight. The invention 10 comprises an accelerometer type acoustic detector 10 including single, dual, or multiple sensors that produce electrical signals representing the cardiac bio-acoustic information. The sensors comprise two low-mass, substantially planar, flexible bending beams 24,26 that each support two mechanically sensitive transducers 16,18,20,22. Said mechanically sensitive transducers 16,18,20,22 are electrically connected to the preamplifier through flexible wires 62. The bending beams 24,26 are attached on each side to lightweight support walls 40,42 and are mechanically coupled through coupling element 30. The right support wall 40 and a left support wall 42 are in turn supported by a support frame 12 which is attached to the patient contact plate 14. Electrical signals 32 are connected through cable 36 and are the outputs of the cardiac acoustic detector 10.

The two bending beams 24, 26 are coupled at the center by a coupling element 30, so both bending beams 24,26 are subject to the same bending action. A coupling element 30 couples the influence of the preamplifier 60 to the lower bending beam 26. Both bending beams 24,26 are center-loaded by the preamplifier 60, such that the bending beams 24,26 respond similarly to accelerations produced by vibrations of the patient's chest.

The support frame 12 is mechanically connected to the patient's chest through a patient contact plate 14 that extends below the support frame 12. The patient contact plate 14 is configured so that a patient's chest vibrations deflect the bending beams 24,26 in accordance with the patient's heart vibrations.

FIG. 6 illustrates one embodiment of the invention 10, including end-loaded low-mass weights 64. The invention 10 comprises an accelerometer type acoustic detector 10 including single, dual, or multiple sensors that produce electrical signals representing the cardiac bio-acoustic information. The sensors comprise two low-mass, substantially planar, flexible bending beams 24,26 that each support two mechanically sensitive transducers 16,18,20,22. Said bending beams 24,26 are mechanically connected through coupling element 30 and are supported by support beam 66 and patient contact plate 68.

Electrical signals 32,34 connected through cables 36,38 are outputs of the cardiac acoustic detector 10.

The two bending beams 24, 26 are coupled at the center by a coupling element 30, so both bending beams 24,26 are subject to the same bending action. A coupling element 30 couples the influence of the low mass weights 64 to the lower bending beam 26. Both bending beams 24,26 are end-loaded by the low mass weights 64, such that the bending beams 24,26 respond similarly to accelerations produced by vibrations of the user's chest. Each bending beam 24,26 could be end-loaded with low-mass weights 64 and supported through support frame 66 and patient contact plate 68.

The support frame 66 is mechanically connected to the patient's chest through the patient contact plate 68 that extends below the support frame 66. The patient contact plate 68 is configured so that a patient's chest vibrations deflect the bending beams 24,26 in accordance with the patient's heart vibrations.

The invention 10 is typically operated by medical personnel who are performing various types of cardiac testing involving sounds produced by a patient's heart. During operation of the invention 10, the user is provided, either by a display unit (not shown) or by other methods, the signal-to-noise ratio for the cardiac bio-acoustic signals received from the accelerometer detector attached to the patient's chest (FIG. 3). By obtaining an accurate measurement of the signal-to-noise ratio, the invention 10 user may thus determine if the quality of the bio-acoustic cardiac signals meets the requirements for the medical test being conducted.

While embodiments of the invention 10 have been described in detail above, the invention 10 is not limited to the specific embodiments described above, which should be considered as merely exemplary illustrations set forth for a clear understanding of the principles of the invention 10. Further variations, modifications, extensions, or equivalents of the invention 10 may be developed without departing from the scope of the invention 10. It is therefore intended that the invention 10 not be limited to the particular embodiments disclosed as the best mode contemplated for carrying out this invention 10, but that the invention 10 will include all the embodiments falling within the scope of the appended claims.

What is claimed is:

1. An apparatus for detection of cardiac acoustic signals, comprising:
at least two mechanically sensitive transducers configured to produce at least two separate electrical output signals in response to the same mechanical inputs;
at least two accelerometer detectors coupled to said mechanically sensitive transducers;
a supporting frame; and
a patient contact plate;
wherein cardiac acoustic signals from a patient may be detected non-invasively.

2. The apparatus of claim 1, wherein said accelerometer detectors comprise flexible, planar bending beams.

3. The apparatus of claim 1, wherein said at least two mechanically sensitive transducers comprise two mechanically sensitive transducers facing upwards and two mechanically sensitive transducers facing downwards.

4. The apparatus of claim 1, wherein said at least two mechanically sensitive transducers are configured to provide at least two separate, single-ended, unipolar output signals.

5. The apparatus of claim 1, wherein said mechanically sensitive transducers comprise piezoelectric materials.

6. The apparatus of claim 1, wherein said mechanically sensitive transducers are selected from the group consisting of piezoelectric ceramics, piezoelectric crystals, piezoelectric film, piezo-resistive material, and strain gages.

7. The apparatus of claim 1, wherein said at least two mechanically sensitive transducers are configured to produce differential electrical output signals providing increased sensitivity and reduced electrical noise.

8. The apparatus of claim 1, wherein said at least two mechanically sensitive transducers comprise one mechanically sensitive transducer configured on an upper surface of at least one said accelerometer detector, and one mechanically sensitive transducers configured on a lower surface of one said accelerometer detector, wherein said mechanically sensitive transducers each produces a single-ended, unipolar output signal.

9. The apparatus of claim 1, wherein said at least two mechanically sensitive transducers are configured on the upper and lower surfaces of said accelerometer detectors so that a force on one said accelerometer detector causes one or more said mechanically sensitive transducers to be in tension and one or more said mechanically sensitive transducers to be in compression.

10. The apparatus of claim 1, wherein said at least two mechanically sensitive transducers are center loaded by one or more low-mass weights.

11. The apparatus of claim 10, wherein said low-mass weights comprise miniaturized electronic components configured as preamplifiers for said at least two mechanically sensitive transducers.

12. The apparatus of claim 1, wherein said accelerometer detectors are end-loaded by a plurality of low-mass weights.

13. The apparatus of claim 1, wherein the resonant frequency of said at least two accelerometer detectors are configured in a range of 800 Hz to 1200 Hz so as to provide increased sensitivity to high frequency heart sounds.

14. The apparatus of claim 1, wherein said at least two accelerometer detectors comprise low-mass accelerometer detectors configured for increased sensitivity at high output frequencies.

15. An apparatus for detection of cardiac acoustic signals, comprising:
at least two mechanically sensitive transducers comprised of piezoelectric materials and configured to produce at least two separate differential, electrical output signals in response to the same mechanical inputs;

at least two accelerometer detectors, configured for increased sensitivity at high output frequencies, and coupled to said mechanically sensitive transducers;

one or more low-mass weights configured to center-load said mechanically sensitive transducers;

a supporting frame; and a patient contact plate;

wherein cardiac acoustic signals from a patient may be detected non-invasively.

16. An apparatus for detection of cardiac acoustic signals, comprising:

one or more acoustic sensors configured to produce electrical output signals in response to mechanical inputs;

one or more bending beams supporting said acoustic sensors;

one or more miniaturized electronic components configured as low-mass weights to center-load said acoustic sensors;

a supporting frame; and a patient contact plate;

wherein cardiac acoustic signals from a patient may be detected non-invasively.

* * * * *